US012606785B2

(12) United States Patent
Heese et al.

(10) Patent No.: US 12,606,785 B2
(45) Date of Patent: Apr. 21, 2026

(54) INSTALLATION FOR BIOTECHNOLOGICAL APPLICATIONS, WITH CARRIER FOR THE MOUNTING OF COMPONENTS

(71) Applicant: Sartorius Stedim Biotech GmbH, Göttingen (DE)

(72) Inventors: Robin Heese, Bebra (DE); Andreas Klemm, Kassel (DE); André Grebe, Malsfeld (DE); Michael Rodenberg, Hannover (DE)

(73) Assignee: Sartorius Stedim Biotech GmbH, Gottingen (DE)

( * ) Notice: Subject to any disclaimer, the term of this patent is extended or adjusted under 35 U.S.C. 154(b) by 286 days.

(21) Appl. No.: 18/491,110

(22) Filed: Oct. 20, 2023

(65) Prior Publication Data

US 2024/0043780 A1    Feb. 8, 2024

Related U.S. Application Data

(62) Division of application No. 16/097,376, filed as application No. PCT/EP2017/000342 on Mar. 16, 2017, now Pat. No. 11,795,425.

(30) Foreign Application Priority Data

Jul. 15, 2016    (DE) .......................... 102016008655.6

(51) Int. Cl.
C12M 1/00    (2006.01)
C12M 3/00    (2006.01)

(52) U.S. Cl.
CPC ............ *C12M 23/46* (2013.01); *C12M 23/28* (2013.01); *C12M 23/48* (2013.01)

(58) Field of Classification Search
CPC ....... C12M 23/28; C12M 23/46; C12M 23/48
See application file for complete search history.

(56) References Cited

FOREIGN PATENT DOCUMENTS

WO        WO-0066706 A1 * 11/2000    ............ B01F 35/513
WO        WO-2016008556 A1 *  1/2016    ............ C12M 23/14

* cited by examiner

*Primary Examiner* — Lydia Edwards
(74) *Attorney, Agent, or Firm* — Quinn IP Law

(57) ABSTRACT

A method for mounting at least one component on an installation includes attaching a carrier directly or indirectly to the installation, where the installation has at least one frame with at least two arms, at least one base plate, and at least one deformable element. The method further includes displacing the component toward the deformable element such that the deformable element is displaced from a receiving state (AUZ), in which the deformable element is ready to receive the component of the installation, toward a locked state (ARZ), as a result of which the deformable element surrounds and mounts the component of the installation at least in part.

7 Claims, 8 Drawing Sheets

INSTALLATION FOR BIOTECHNOLOGICAL APPLICATIONS, WITH CARRIER FOR THE MOUNTING OF COMPONENTS

CROSS REFERENCE TO RELATED APPLICATIONS

The present application is a divisional of U.S. patent application Ser. No. 16/097,376, filed 29 Oct. 2018, and published as US 2019/0144811, which is a 371 of PCT/EP2017/000342, filed 16 Mar. 2017, which claims the benefit of priority from German Application 10 2016 008 655.6, filed 15 Jul. 2016. The '376 application is incorporated by reference in its entirety and for all that it discloses.

TECHNICAL FIELD

The present disclosure relates to an installation for biotechnological applications including at least one carrier for the mounting of components of the installation.

BACKGROUND

Installations (e.g. the bioreactors disclosed in WO 2011/134629 or WO 2009/103450) and in particular single-use assemblies regularly include a high number of components which can be lines and sensors which are guided or mounted and/or fixed at predetermined positions and in particular, in this case, are not meant to come into contact with the bottom of the space in which the installation is operated. The trouble-free operation of such installations additionally requires that the components assume a specific arrangement, where the components are, in particular, not bent or permanently deformed and/or damaged.

Up to now lines (hoses, electric lines or cables) and sensors are laid during construction or during the maintenance of installations by means of cable ties or clamps (in particular clamps produced from metal and/or plastics material) and are fastened to the installation. For example, cable ties are used for laying, mounting and fastening lines at such positions of the installation which allow the cable ties to be bound thereto. Cable ties, on account of their narrow contact or support surface, exert high pressure on the corresponding line when the cable tie is tightened for fixing the line such that, as a result, the line can be permanently deformed or bent. To remove the connection, a sharp tool, such as shears or a blade, is necessary, as a result of which the line can be damaged.

As an alternative to this, tri-clamps, which are fastened on the housing or profile of the installation, are also used to fix lines. A connecting portion has to be tightened to close the tri-clamp. Tri-clamps of a predetermined size have proved to be rather inflexible with reference to various hose forms and diameters. A further alternative for fixing lines is provided by mounting systems in which clamps are screwed together, such as, for example, hose clips. The disadvantage of such systems is that a tool is required to operate them. The operation of a tool in this connection often proves to be cumbersome, as the screw head profile of the screws which close the clips are difficult to access. In addition, hose clips can be sharp-edged and the edges thereof can damage the components during fixing. Further alternatives are formed by spring steel clips, plastic material clamps or fixing rings, rings with openings which are usually used for the mounting of lines. However, these solutions also prove to be too cumbersome in practice and damage to the component to be fixed is not excluded.

It is consequently the object of the present invention to ensure efficient operation or efficient commissioning or efficient development of installations, in particular bioreactors and in particular single-use installations.

SUMMARY

The installation for biotechnological applications, which is designated below as the installation, can be, for example, a bioreactor. The installation can be, in particular, single-use installations for biotechnological applications, crossflow installations, bioreactors, biogas installations and/or similar installations. The components to be mounted in or on the installation, in this case, can be, for example, sensors, filters/filter systems, lines, in particular hoses and/or cabling.

The named problem is solved by the features of the independent claims. Advantageous embodiments are the object of the dependent claims.

According to one aspect of the present invention, an installation for biotechnological applications, in particular a bioreactor, is provided, including at least one container and at least one carrier, wherein the carrier is designed for the mounting of at least one component of the installation and the carrier is designed for the purpose of being attached directly or indirectly to the installation, and the at least one carrier includes at least one frame with at least two arms, at least one base plate and at least one deformable element, wherein the deformable element includes fastening portions and wherein the fastening portions are mounted on the arms of the frame and wherein the deformable element is designed for the purpose of assuming at least the following states: a receiving state, where the deformable element is ready to receive the component of the installation and a locked state, which is produced by the displacing of the component of the installation into the deformable element, as a result of which the deformable element surrounds the component of the installation at least in part.

An installation with an improved fastening device or an improved mounting system for guiding and/or mounting components of the installation is correspondingly provided. In particular, in the case of installations with at least one pump, the corresponding inlet and/or outlet line(s) can be mounted suitably in a localized manner by means of the at least one carrier and, in particular, vibrations occurring as a result of the at least one carrier can be damped or substantially prevented. In addition, in particular in the case of an installation such as a bioreactor and in particular a single-use assembly, a large number of components, which can be a line and/or a sensor or lines and/or sensors, can be guided or mounted and/or fixed advantageously and simply at predetermined or predeterminable positions, as a result of which it is possible, in particular, to avoid said components coming into contact with an inner bottom of the installation and/or the bottom of the space in which the installation is operated. In addition, fault-free operation of such installations is advantageously made possible as the components assume a specific arrangement in which the components are, in particular, not bent or permanently deformed and/or damaged. In addition, a plurality of components can be guided in a targeted, ordered and/or efficient manner to various portions of the installation, for example to tanks, to filters and/or to pumps. It is also advantageously possible to attach in particular sensor systems (e.g. pressure and/or throughput sensors) to the installation, substantially without any physical pressure being exerted on them by the carrier. In a preferred manner, on the one hand, the one or multiple components are consequently able to be mounted or held and fixed in a fixed and secure manner and, on the other hand, incorrect stress (crimping and/or pressure) on said components is able to be avoided to avoid malfunctions and/or permanent damage to the components. In addition, vibrations, for example triggered by pumps, are able to be adsorbed by the carrier or the carriers.

In addition, hose assemblies or construction kits including at least one hose and/or another component of the installation are designed in the majority of cases for single-use (i.e. for use in one single process) and are frequently laid by the user himself. Correspondingly, the installation enables quick, uncomplicated and efficient installation and expansion, in particular avoiding the use of tools, as the (single-use) components could be damaged by tools. In addition, the handling of tools is inefficient and uncomfortable for the user (e.g. rotating, screwing or similar). Consequently, tool-free mounting or attaching of the component(s) on or to the installation by means of the carrier is an advantage.

In one embodiment of the installation, the base plate of the carrier can be attached directly or indirectly to the installation so as to be pivotable via a bearing and/or a belt and/or a joint.

There is an advantage in attaching the carrier or the base plate of the carrier as an option directly or indirectly to the installation so as to be pivotable via a bearing and/or a belt and/or a joint, as the carrier can be aligned in the direction in which the component is to be laid in such a manner that kinking or bending of the component is advantageously avoided. As a result of locking the joint, the advantageous alignment of the component (e.g. of the hose or of a sensor device) in the laying direction can additionally be permanently fixed.

In one embodiment of the installation, at least one of the fastening portions can be mounted so as to be slidingly rotatable about a pivot point of a bearing counterpart, which is fixed on at least one of the arms and cannot be rotated in relation to the respective arm, in each case by means of at least one bearing part, preferably a sliding bearing, which is attached on one of the fastening portions.

The optional slidingly rotatable mounting of at least one of the fastening portions via at least one bearing counterpart which is attached to one of the fastening portions, is fixed on the respective arm and is preferably a sliding bearing, has the advantage that the bearing counterpart is able to be realized in one part or integrally with the frame. As the frame is preferably formed from a metal or steel, the bearing counterpart is also formed in a preferred manner from metal or steel and has accordingly (in particular where realized in one part or integrally with the frame) great stability. In addition, where it is realized in one part or integrally with the frame, it is possible to save on the costs of production. This applies, in particular, when the bearing counterpart is a joint or a bolt. In order to achieve greater stability, in particular a metal or steel can be chosen to produce the joint. It is equally conceivable for the joint to be realized integrally with the deformable element when said deformable element is produced from a polymer, e.g. by recasting.

In one embodiment of the installation, a safety element can be arrangeable on the frame and/or on the deformable element in order to prevent the opening of the deformable element in the locked state.

As a result of the optional provision of an additional safety element such as, for example, a belt and/or a clamp and/or a bracket on the frame and/or on the deformable element, the deformable element can be prevented from coming loose (in particular unintentionally) from the locked state and transferring into the receiving state or moving toward said state, as a result of which, the fixing or mounting of the component by the carrier would be impaired or would be lost, which could be triggered, in particular, by strong vibrations or strong flow streams of the liquid in the container.

In one embodiment of the installation, the deformable element can include on its contact surfaces structural elements and/or elevations and/or indentations, which are in at least partial contact with the component of the installation.

As a result of additional optional structural elements which include, for example, elevations and/or indentations, contact or pressure points can be realized which generate reinforced pressure or friction on their contact surfaces with the components in the locked state. Said pressure or friction points cause the components to be mounted in a slip-free manner, or in other words to be held in a more fixed and safer manner by the deformable element.

In one embodiment of the installation, the deformable element can be designed for the purpose of receiving and/or mounting and/or fixing components of the installation with various forms and/or diameters or cross-sectional surfaces.

Universal use of the carrier can be achieved as a result of the deformable element being designed for the purpose of being able to receive components with various forms and/or diameters. In this case, one and the same carrier can be used in a corresponding manner when exchanging different components, which makes exchanging the carrier for a certain dimension superfluous as it is possible to use the carrier in a versatile manner.

In one embodiment of the installation, at least one element included by the installation can comprise at least a color corresponding to a color coding.

A further advantage is to be found in that the optional coloring of the individual elements of the installation and in particular of the mounting system, e.g. of the deformable element, can be subject to a color coding. The color coding can give, for example, information on the receiving capacity of components of a certain cross section or diameter or a certain form. The direction of flow of material through a hose can also be characterized in such a manner.

According to a further aspect of the present invention, a carrier is provided for the mounting of at least one component on an installation, including at least one frame with at least two arms, at least one base plate and at least one deformable element, wherein the deformable element includes fastening portions and wherein the fastening portions are mounted on the arms of the frame and wherein the deformable element is designed for the purpose of assuming at least the following states: a receiving state, where the deformable element is ready to receive the component of the installation, and a locked state, which is produced by the displacing the component of the installation into the deformable element, as a result of which the deformable element surrounds the component of the installation at least in part.

Provided in particular is a carrier which is designed for the purpose of mounting at least one component of an installation, and wherein the carrier is additionally designed for the purpose of being attached directly or indirectly to the installation.

In one embodiment of the carrier, the base plate is attachable directly or indirectly to the installation by means of a bearing and/or a belt and/or a joint so as to be pivotable.

According to a further aspect of the present invention, a method is provided for the mounting of at least one component on an installation, in particular according to the preceding aspect of the invention or a preferred embodiment thereof, wherein the method comprises the following steps:

attaching a carrier, in particular according to the preceding aspect of the invention or a preferred embodiment thereof, directly or indirectly to the installation which includes at least one frame with at least two arms, at least one base plate and at least one deformable element, displacing the component toward the deformable element such that the deformable element is displaced from a receiving state, in which the deformable element is ready to receive the component of the installation, toward a locked state, as a result of which the deformable element surrounds the component of the installation at least in part and mounts it.

The rapid and simple handling of one of the embodiments of the carrier for repeated use (laying, mounting, fixing, releasing, removing, exchanging of components of an installation) by hand is advantageous compared to the conventional fastening methods of components, as the user does not require a tool for the operation and use thereof. The user can "click" on a component with a simple movement, as a result of which said component is then mounted or held. The component is released from the holder only when the user pulls said component with some force out of the deformable element which surrounds it at least in part (pulling it out of the carrier perpendicular to the longitudinal axis of the component). The system is based on a simple mechanism and consequently makes the use of a tool superfluous. The components are consequently not damaged by the use of a tool. The user is additionally able to lay, mount, fix, align, remove and exchange a plurality of components in a very efficient and quick manner.

In addition, the advantage of using the carrier is that no sharp edges or similar danger points are present as a result of which the components to be mounted and fixed could be damaged, or as a result of which the user could be injured during operation.

The components of the installation can be clamped into the carrier, as a result of which the components, e.g. hoses, are prevented from "sagging" loosely and thus being susceptible to faults in the case of vibrations. In this case, vibrations, oscillations and pulsations, which are possibly triggered by the pumps of the installation, are adsorbed and damped by the carrier. This is particularly advantageous when the carrier is to be used to hold sensors, as oscillations and vibrations are prevented from being transmitted between different components of the sensor. The transmission of vibrations to a sensor or a sensor head could influence, falsify the measuring signal and produce interfering signals.

The mounting system and in particular the carrier can also be used advantageously as an alternative to this in the following regions: laboratory equipment, chemical production installations, pharmaceutical production installations, medical diagnostic devices, reactors in general, devices which are based in general on principles of physics and include a high number of components such as lines and cables, and computer centers. In particular, the embodiments of the carrier and of the mounting system described herein are suitable for use in connection with single-use installations or single-use systems.

A versatile use of the carrier for the holding and mounting of components, such as cables, thin filter capsules or small delivery receptacles provides a further advantage. In addition, the described embodiments of the carrier can be used anywhere where hoses, sensors, cables, (optical and/or electric) signal cable, lines, filter capsules, small receptacles or similar are to be guided and/or mounted. Such systems include, for example, FlexAct, SartoflowCrossflow installations, BIOSTAT STR, Pallentank or fluid management.

Further features, advantages and functions are described in detail below by way of particular embodiments. Although individual embodiments are described separately, individual features thereof can be combined to form further embodiments.

DETAILED DESCRIPTION

The figures include marked axes with directions which are characterized by arrows and reference symbols x, y, z. Said axes relate in each case to the objects shown and are to be understood individually and independently for each figure.

Figure 1:
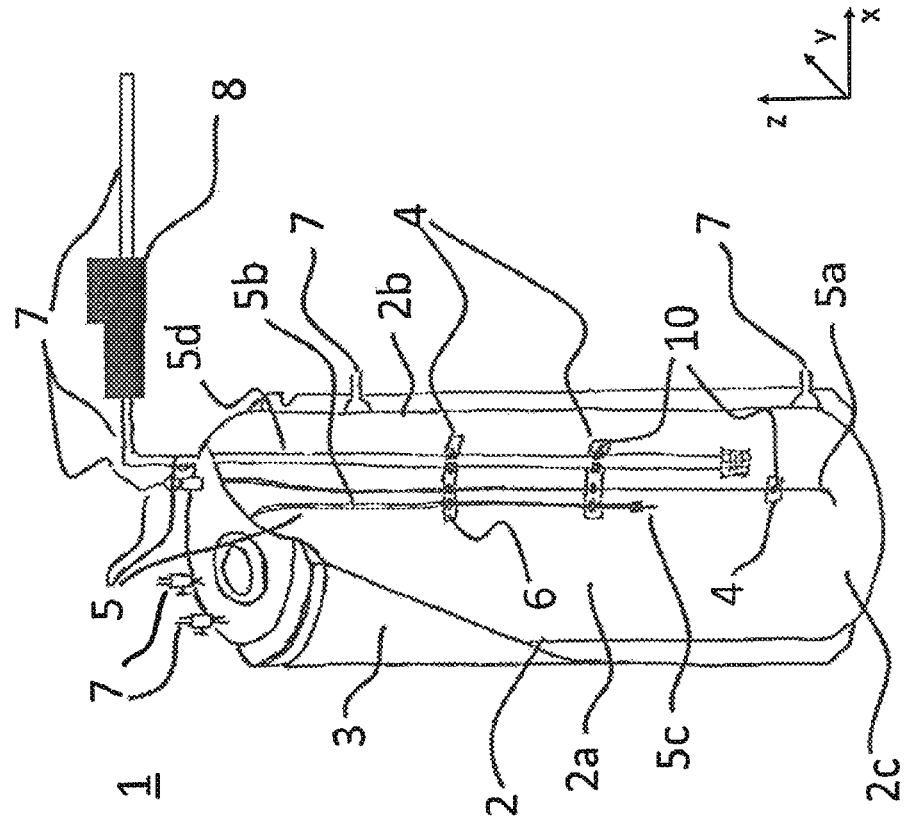
FIG. 1 is a schematic partially broken-open representation of the inside and outside of an installation according to a first embodiment.

FIG. 1 shows a (partially broken-open) exemplary representation of the outside and inside of an installation 1. The installation 1 can be, in particular, single-use installations for biotechnological applications, crossflow installations, filtration installations, bioreactor containers, biogas installations, mixers or mixing systems, shakers, freezing and thawing containers, devices for treating fluids and/or similar installations. In particular, an installation for biotechnological applications comprises at least one pump and/or at least one transfer line.

In addition, installations for biotechnological applications (e.g. bioreactors) include, in particular, containers in which specially grown microorganisms and/or cells are cultivated in a culture medium under as optimally controlled conditions as possible in order to obtain either the cells themselves, parts thereof and/or one of their metabolic products. To this end, one or multiple inlet and outlet lines are required for the respective individual products or materials. Solid (biomass), liquid (culture medium) and/or gaseous (e.g. air, oxygen, carbon dioxide, nitrogen) phases can be processed in the installations especially.

In order to ensure optimum conditions, one or multiple (different) parameters are usually measured or monitored in the interior of the installation by means of sensors 5c which project into the interior of the installation. Possible parameters to be measured are, for example, the pH value, the O2 value and the temperature of the medium included in the installation. Should parameters deviate from predefined optimum values, it is possible to correct the deviations by means of suitable measures. Installations can be designed for repeated use or as a disposable installation or disposable bioreactor. If it is a disposable installation, or disposable bioreactor, these are often already produced together with one or multiple sensor(s) at the factory and are then delivered to the user as a sterile unit. Once the disposable installation or the disposable bioreactor has been utilized, the sensor can be disposed of together with the installation or the bioreactor. The sensor is consequently a disposable sensor.

The installation 1 includes a container 2, in particular in the form of a disposable bag, an interior of the container 2a, a container inside wall 2b, and inside bottom 2c of the container 2, a container frame 3, one or multiple pumps 8 or pump systems, one or multiple entries and/or exits 7, through which substances can be introduced to or removed from the system, and/or at least one mounting system 4.

The mounting system 4 serves for the at least partial mounting of one or multiple components 5 of the installation 1, in particular of the bioreactor 1, inside and/or outside the container 2 and/or on the container frame 3. Such components 5 of the installation 1 can be one or multiple lines such as, for example, hoses 5a, electric cable 5b and/or pipes 5d. The components 5 can also include sensors 5c and/or shanks of other components 5 or elements of the installation 1. The mounting system 4 includes at least one or multiple carriers 10 or holders or mountings.

A carrier 10 is designed for the purpose of receiving, mounting and/or fixing one or multiple components 5 of the installation 1 at least in part. The carrier or carriers 10 can be attached or fastened either directly or indirectly to the installation 1. For example, a carrier 10 can be bonded (adhesively) and/or screw-connected and/or magnetically connected to the installation 1. As an alternative to this or in addition to it, a carrier 10 can be indirectly attached to the installation 1. To this end, the mounting system 4 can include, as an option, a fastening system 6 which can comprise, for example, a jaw 6a, and/or another connection part and a mounting 6b. The mounting 6b can comprise, for example, a rail or a mounting 6b with a click connection. The corresponding counterpart of the mounting can be situated on the connection part of the carrier 10 and/or on the jaw 6a for the (in particularly direct) connection on the carrier 10. For example, the mounting 6b can include a journal which interacts with an opening on the connection part.

For indirect attachment to the installation 1, a carrier 10 is connected to a connection part (e.g. the jaw 6a). The carrier 10 can then be connected via the connection part, for example via the jaw 6a, to the corresponding mounting 6b, namely the rail. The mounting 6b (here in particular the rail) is attached for this purpose to the installation 1. The mounting 6b is designed for the purpose of receiving one or multiple carriers 10 or one or multiple connection parts with the corresponding carriers 10 (in a preferred manner so as to be displaceable or slidable). The mechanism, on which the connection between carrier or connection part and mounting is based, includes in particular: click connections, rail systems, screw connections, magnetic and/or adhesive connections. The mounting 6b itself can also be attached to the installation 1 via one of the named mechanisms.

The mounting system 4 is in particular suitable for holding and/or fastening or fixing components 5 in a single-use installation. For example, by means of the mounting system 4, one or multiple components 5 can be laid, moved and/or fixed in such a manner at predetermined positions that, in so doing, they are not or do not come into contact in particular with other components 5 and/or, for example, with the inside bottom of the container 2c. In addition, in this way the components 5 can be laid in an efficient, sorted and/or space-saving manner.

Figures 2A, 2B:
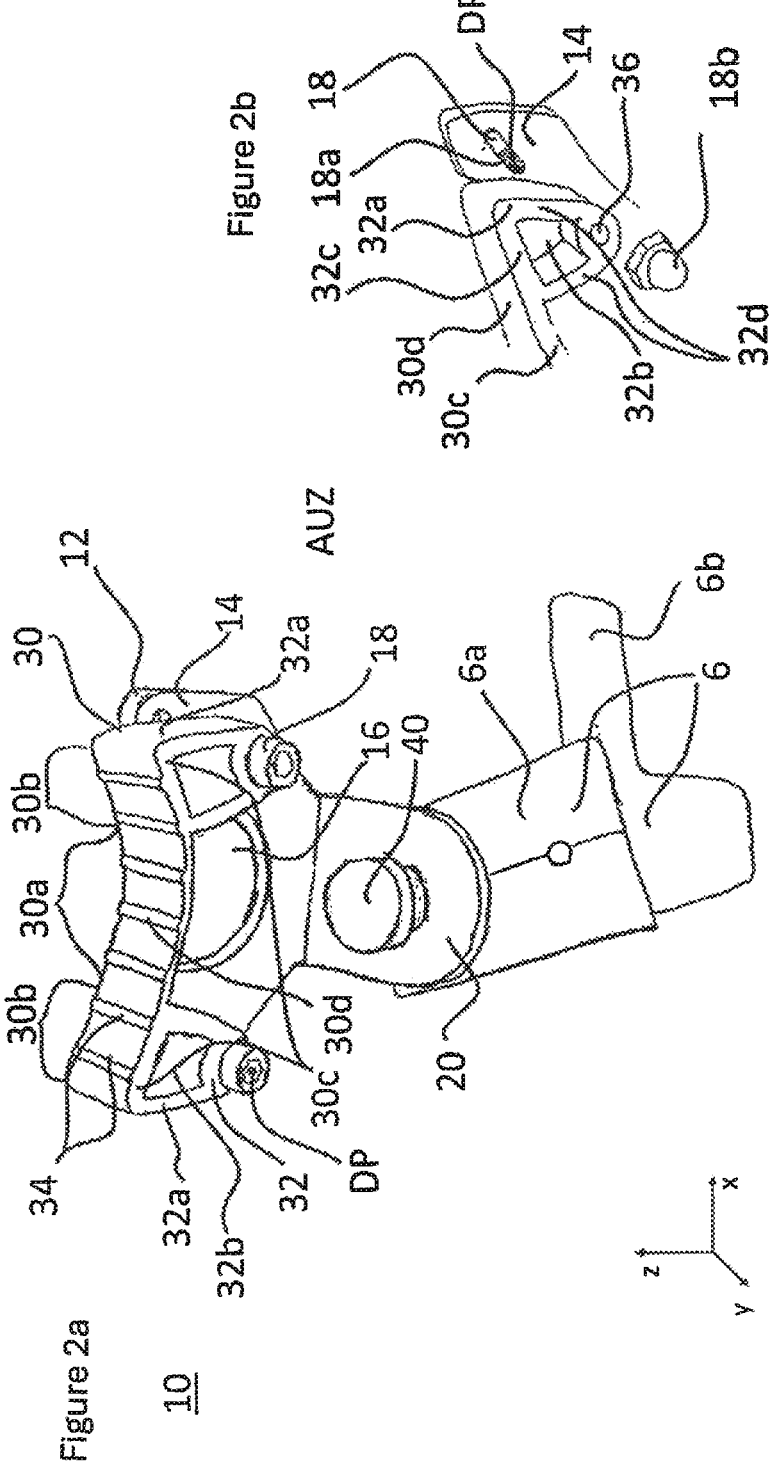
FIG. 2a is a perspective rear view of a carrier in the receiving state.
FIG. 2b is an exploded view which shows a schematic representation of a detail of the mounting of a fastening portion as an example.
Figure 3:
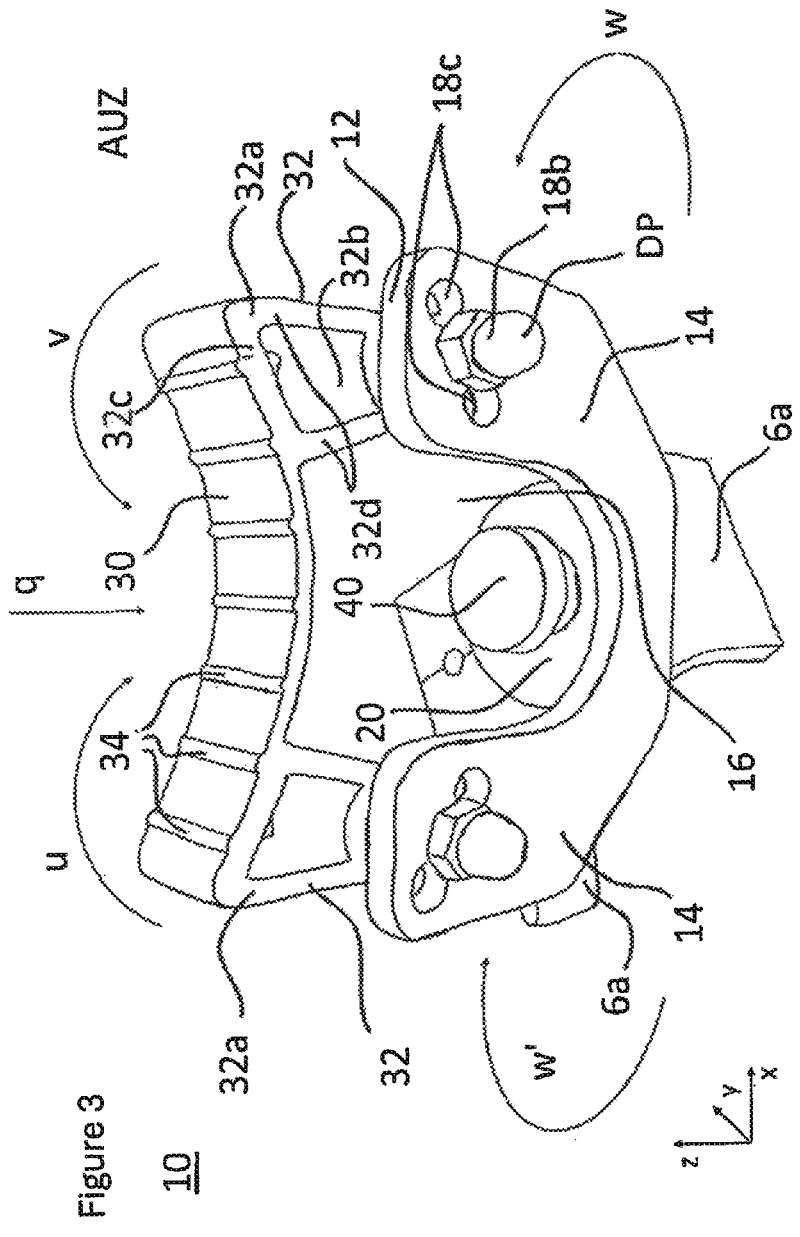
FIG. 3 is a perspective front view of a carrier in the receiving state.

FIGS. 2a and 3 show in each case a perspective rear view and a perspective front view of a preferred carrier 10 in a receiving state AUZ. The carrier 10 includes a frame 12. As an alternative to this, the carrier 10 can also include more than one frame 12. The frame 12 is realized in a substantially U-shaped or alternatively V-shaped manner and comprises two arms 14 which surround or define a recess 16 at least in part. As an alternative to this, the frame 12 can also comprise more than two arms 14 which surround more than one recess 16.

The carrier 10 additionally includes a base plate 20 which extends, in particular, at an angle which is smaller than 180° and greater than 0° (in a preferred manner is approximately 90°) from the frame 12 (in particular at the distal end thereof opposite the arms 14). As an alternative to this, the carrier 10 can also be realized without a plate or base plate 20.

In addition, the carrier 10 includes a deformable element 30 which includes a deformable portion 30a and two rigid portions 30b. As an alternative to this, the deformable element 30 can also include more than one deformable portion 30a and/or only one rigid portion 30b or more than two rigid portions 30b.

The deformable element 30 also includes a contact portion 30c, preferably in the form of a belt, the contact portion 30c being designed for the purpose of moving into contact at least in part via a contact surface 30d with the component 5 of the installation 1. The contact surface 30d of the deformable element 30, which moves into contact with the component 5 of the installation 1 at least in part, can include one or more structural elements 34. Such structural elements 34 can comprise, in particular, elevations and/or indentations, struts and/or nubs, and/or other structures.

The structural elements 34, however, can also be realized laterally, that is to say in the plane of the contact surface 30d. In other words, the structural elements 34 can give the belt or the contact portion 30c a lateral edge structure. The surface of the contact surface 30d, which (in the locked state ARZ) is actually in (or can move into) contact with the component 5, can be defined, depending on the realization, on the one hand, by the surfaces of the structural elements 34, that is to say the pressure points, or can include, at least in part, at least one contiguous and/or continuous surface of the contact surface 30d, which proceeds beyond the surfaces of the structural elements 34. In FIGS. 2a, 3, 6 and 7, the structural elements 34 are realized as struts which are raised from the belt surface or contact surface 30d and extend perpendicularly to the long side of the belt.

The deformable element 30 in FIGS. 2a, 2b and 3 is shown in the receiving state AUZ. Said receiving state AUZ is distinguished in particular in that no components 5 of the installation 1 have been received yet by the carrier 10. The deformable element 30, in this case, stands ready to receive a component 5 of the installation 1.

The deformable element 30 additionally includes fastening portions 32. The fastening portions 32 are preferably situated at both ends of the belt, i.e. at the ends of the contact portion 30c which moves into contact at least in part with the component 5 of the installation 1. In addition, the fastening portions 32 preferably extend at an angle which is greater than 0° and smaller than 180° (in a preferred manner is approximately) 90° from the contact portion 30c of the deformable element 30.

The fastening portions 32 are preferably pivotably mounted in each case on the arms 14 of the frame 12. FIG.

2b is a perspective image of a detail of a fastening portion 32, as is shown in FIG. 2a. FIG. 2b shows a schematic representation as an example of the mounting of the fastening portion 32 on a frame 12. In this case, at least one of the fastening portions 32 can be mounted on in each case one of the arms 14 of the frame 12 so as to be rotatable or displaceable about in each case a rotational axis or a pivot point DP. This preferably applies to both fastening portions 32. To this end, the fastening portions 32 each include a portion for a bearing system including a bearing part 36 which is compatible with a bearing counterpart 18, attached to the frame 12, preferably on one of the arms 14 of the frame 12.

The embodiment shown as an example in FIG. 2b includes a bearing part 36 on the fastening portion 32, which bearing part is a continuous bore or recess in this example, and a bearing counterpart 18 which is situated on the frame 12 and comprises in this example in particular a pin or a joint or a bolt. In particular, the counter bearing part 18 is produced from metal or steel and is realized integrally or in one part with the corresponding arm 14 (e.g. the bearing part 18 is welded to the arm 14).

The bearing part 36 can also include, however, an (in particular reinforced) sleeve and/or an at least partially recessed portion or a cavity or a trough in the fastening portion 32 which surrounds the bearing counterpart 18 at least in part. The bearing part 36 can additionally also include a ball bearing, a sliding bearing and/or a similar bearing or a joint-receiving portion. The pin or the joint is preferably mounted in a fixed manner on the frame 12 (in the embodiment of FIG. 2b) and consequently forms a fixed non-rotatable joint which cannot rotate in relation to the arm 14. The pin 18 can include a thread 18a and/or can be guided at least in part through the through-bore or the bearing part 36 or the joint-receiving portion (or can be received therein) and in particular can be closed by means of a closing element 18b which, is shown in the present case in particular as a nut with a threaded counterpart.

According to FIGS. 2a and 3, the joint 18 includes in particular a screw which is fixed to the frame 12 (e.g. as a result of welding) and is closed off by means of a nut 18b on the thread 18a. Where required, the position of the bearing counterpart 18 can be modified by displacement on or along an (in particular different) displacement recess 18c. In particular, the displacement recess 18c is realized as an elongated hole or slot or elongated bore. This allows the contact surface 30d and the pressure on the component 5 to be varied. After the deformable element 30 has been received by the pin 18 and closure has occurred by means of the nut 18b, the fastening portion 32 can be rotated in particular about the rotational axis or the pivot point DP defined by the pin in relation to the bearing counterpart 18 and the frame 12.

Consequently, at least one of the fastening portions 32, but preferably both fastening portions 32 of the deformable element 30 can each be mounted so as to be slidingly rotatable about in each case a pivot point DP or rotational axis via at least one fixed bearing counterpart 18, which is attached or fixed in each case on at least one of the arms 14 on the frame 12.

As an alternative to this, the bearing part 36 can, however, also include either a pin or joint and/or can be connected to a pin in such a manner that a rotation of the fastening portion 32 toward the pin or the joint is not possible. The bearing counterpart 18, in said alternative case, then includes a receiving portion or a joint receiving portion which is able to mount the pin or the bearing part 36 so as to be rotatable and/or pivotable (at least in part). The receiving portion of the bearing counterpart 18 can include a recess or a through-bore in the frame 12 and/or a ball bearing or sliding bearing or a similar bearing. In this case, the fastening portion 32 with the fixed pin rotates or pivots toward the bearing counterpart 18 about a rotation or pivot point DP and/or a rotational axis. In other words, the joint 36 fixed on one of the arms 14 can rotate together with the fastening portion 32 about the pivot point DP. The rotatable/pivotable mounting is ensured by the bearing counterpart 18 on the frame 12. Bearing part 36 and bearing counterpart 18—insofar as they are not simply recesses—can include a plastics material, e.g. a polymer and/or a metal or a combination or a mixture thereof. For example, in the case of a ball bearing, the ball can be metal and the mounting or the bearing of the balls can be produced from a polymer.

In this case, at least one of the fastening portions 32 can comprise at least one leg 32a, preferably both fastening portions 32 each include at least one leg 32a. The leg 32a additionally has the portion which is mounted or fixed so as to be rotatable or displaceable in each case on one of the arms 14 of the frame 12 and accordingly includes a rotational axis with reference to the pivot point DP or to the rotational axis and, when exercising a rotation, has a torque. In particular, the fastening portion 32 comprises two struts or strips 32d which are spaced apart from one another in a region and realize a recess 32b between them and join together in another region in the vicinity of the joint 36. The two struts or strips 32d, with a region 32c which bridges them, consequently form the rigid portion 30b of the deformable element 30 which consequently comprises, in particular, a substantially triangular shape.

It is equally possible for the carrier 10 also to be designed for the purpose of receiving and mounting more than one component 5. To this end, the frame 12 can be realized in particular in a substantially W-shaped and/or Z-shaped manner and/or comprise more than two arms 14, and correspondingly more than one recess 16. In addition, the carrier 10 comprises more than one deformable element 30 and/or a deformable element 30 with more than two fastening portions 32. The adjacent ends of two deformable elements 30 can then be mounted on a common arm 14.

As an alternative to this, one or both of the fastening portions 32, however, can also be situated directly on the respective end of the contact portion 30c which moves into contact with the component 5 of the installation 1 at least in part without it extending therefrom at an angle which is greater than 0° and smaller than 180° (in particular is approximately 90°). In this case, the fastening portion 32 can be fixed in such a manner that there is no rotatable mounting on such a fastening portion 32. The receiving of components 5 consequently does not presume in particular any rotating mechanism of the fastening portions 32 but simply requires that the deformable element 30 deforms in the locked state ARZ in such a manner that sturdy fixing of the component 5 can be ensured.

The deformable portion 30a of the deformable element 30 comprises at least a material with deformable, in particular flexible characteristics. The material of the deformable element 30 can include a plastics material or a mixture of plastics materials, a polymer and in particular a thermoelastic elastomer (TPE), but also metals or alloys. The deformable element 30 is preferably realized from TPE as said material comprises material resistance against acids and alkalis as well as some organic solvents. In addition, TPE is resistant to cleaning and sterilizing by dishwasher or autoclaves or (vapor) sterilizers.

The deformable element 30 can also be realized in part from one of the named materials and in part from another of the named materials. The use of a combination of various materials is advantageous in particular when a portion of the deformable element 30, which is preferably the fastening portion 32, is to have rather rigid or non-deformable characteristics, whilst another portion, which is preferably the deformable portion 30*a* which includes the contact portion 30*c* and moves into contact at least in part with the component 5 of the installation 1, is to have rather deformable characteristics. Improved stiffness or rigidity of the fastening portions 32 or of the legs 32*a* can also be obtained as a result of realizing them in a sturdy form. Such a form can include, for example as shown in FIG. 3, two struts 32*d* which are spaced apart from one another and surround a recess 32*b* of the leg 32*a* or a cavity at least in part. As an alternative to this, said cavity can also be filled such that the fastening portion 32 does not include any struts 32*d* but rather a solid portion (not shown).

The circumference of the (preferably circular) receiving means of a component 5 is determined over the length of the deformable element 30, as a result of which is determined which cross section or which diameter D of a component 5 is able to be received and mounted. The deformable element 30, in this case, can provide flexibility or tolerance, a deformable element 30 of a certain length being able to mount variously sized components 5 with various cross-sectional areas. The deformable element 30 can be designed variously in its dimension and its form, depending on which specific function is to be achieved. For example, in the case of a simple carrier 10, only one deformable element 30 is provided. If said principle is to be used to mount a sensor 5*c* (e.g. within a hose opening), it is thus advantageous to hold the respective hose end on both sides of the sensor 5*c*. It is advantageous for this when the carrier 10 includes two deformable elements 30 arranged one behind the other (cf. e.g. FIG. 5 which is described in more detail below). One of the deformable elements 30 can accordingly mount the hose end and the other deformable element 30 could mount the sensor 5*c*.

The frame 12 of the carrier 10 can be formed from at least one plastics material, polymer, a metal and/or an alloy, preferably from stainless steel and/or can be realized in one part or integrally or can consist of multiple elements. The frame 12 can also be realized from a combination of elements produced from various metals, alloys and/or various plastics materials. The base plate 20 can also be realized in one part with the frame 12 or it can be present as a separate element which is connected or can be connected to the frame 12. The frame 12 is preferably realized from stainless steel, as a result of which the material is steadfast against cleaning and autoclaving in dishwashing machines and autoclaves or (vapor) sterilizers.

The carrier 10 can be attached to the installation 1 with or without a base plate 20 either directly or by means of a fastening system 6. For the case where the carrier 10 includes a base plate 20, the fastening can be effected via the base plate 20. Where the carrier 10 is fastened directly to the installation 1, the carrier 10, with and/or without a base plate 20, can be screw-connected to an element of the installation 1, can be connected or fixed by means of an adhesive means such as, for example, an adhesive, and/or by means of a magnetic system.

Figure 8:
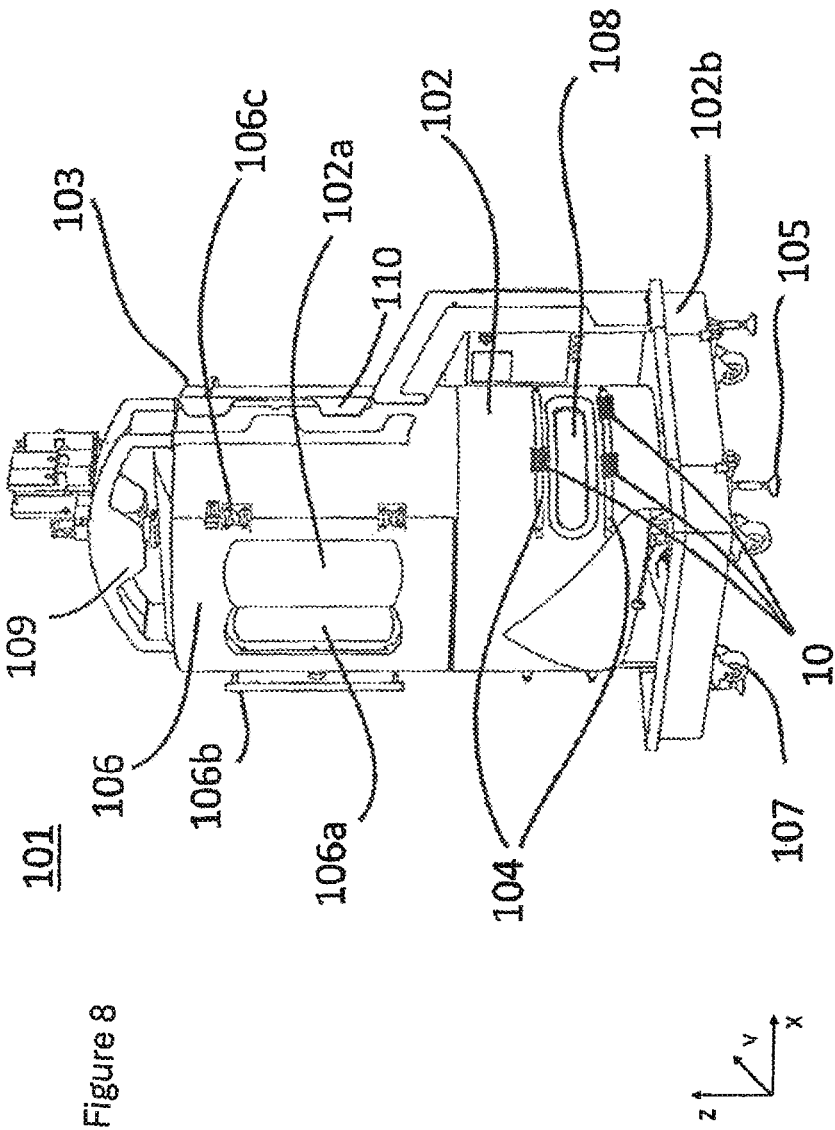

An advantage of using a base plate 20 consists in the simplified handling. For example, when the base plate 20 is screw-connected to the installation 1, screw heads can be recessed in recesses in the base plate 20. Said screw heads are correspondingly easily accessible for the user. If the carrier 10 is to be attached to the installation 1 by means of a fastening system 6, the carrier 10 can thus be connected, for example, with and without base plate 20, to a jaw 6*a* which can be attached and/or fixed to a mounting 6*b* such as, for example, a system rail 104, as shown in FIG. 8. The mounting 6*b*, in this case, is attached directly or indirectly to the installation 1. The fastening system 6, in this case, can include a modular system which is designed for the purpose of receiving a number of carriers 10 which changes or is not fixed beforehand.

The carrier 10 can be pivotably and/or rotatably mounted on the fastening system 6 or the installation 1 or an element of the installation 1 via the base plate 20 by means of a pivoting mechanism which includes a bearing, a belt and/or a joint 40, for example a ball joint. As shown in FIG. 3, the carrier 10 is mounted on a jaw 6*a* of the installation 1 so as to be rotatable and/or pivotable by means of a base plate 20, in particular via a joint 40. The carrier 10 can be rotated via said rotating and/or pivoting mechanism clockwise or anti-clockwise (in each case characterized by the reference symbols w' and w and the associated arrows) about the rotational or pivot axis of the bearing or of the joint 40 in relation to the fastening system 6 or with direct connection in relation to the installation 1. As a result of the rotating and/or pivoting, it is advantageously possible for the component 5, which can be, for example, a hose 5*a*, to be able to be aligned in the laying direction when being laid without the component 5 being bent at the same time. The desired alignment of the component 5 can not only be modified but can also be fixed on the bearing or joint by means of an adjusting/fixing screw. Accordingly, very targeted guiding of the hose can be achieved.

The state shown in FIG. 3, which corresponds to the receiving state AUZ, is distinguished in that, in the case of a rotatable mounting, the fastening portions 32 of the deformable element 30 are generally speaking remote from one another. In this case, the contact surface 30*d* of the portion which moves into contact with the component 5 of the installation 1 at least in part, is aligned opposite the recess 16 (corresponds to the z direction of the z axis shown in FIG. 3 or "upward"). The contact portion 30*c*, which moves into contact at least in part with the component 5 of the installation 1 over the contact surface 30*d*, is aligned generally speaking in the z direction of the z axis shown in FIG. 3 ("upward"). The recess 16 of the frame 12 is consequently surrounded by the deformable element 30 at least in part.

Figure 4:
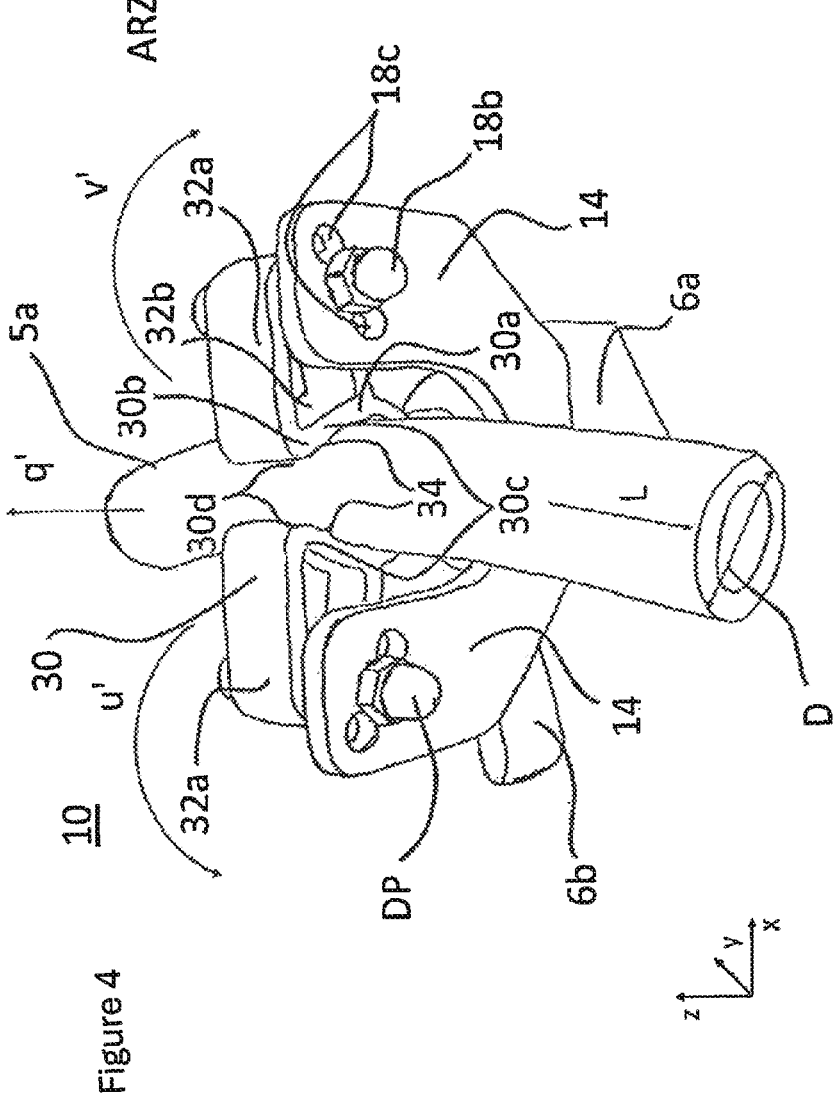
FIG. 4 is a perspective front view of a carrier in the locked state with a fixed hose.

The receiving state AUZ can be transferred into a further different state which corresponds to the locked state ARZ. The perspective front view of a carrier 10, which is situated in the locked state ARZ, is shown in FIG. 4. The transition from the receiving state AUZ into the locked state ARZ can be achieved as a result of a component 5 of the installation 1, such as, for example, a hose 5*a*, being displaced onto or pressed into (in particular substantially centrally) the contact surface 30*d* of the portion, which moves into contact at least partially with the component 5, in the direction of the recess 16. The direction in which the component 5 is displaced relative to the recess 16 is characterized in FIG. 3 by way of an arrow q. The pressure which is exerted via the component 5 onto the contact portion 30*c* of the deformable element 30 for example by a user, triggers a rotational movement of the fastening portions 32 about the respective bearing axis or pivot point DP of the bearing formed by the bearing counterpart 18. The rotation is effected toward the recess 16 for the corresponding fastening portions 32. The directions of rotation of the fastening portions 32 are characterized in FIG. 3 by way of arrows and the associated reference symbols u and v. As an alternative to this, the fastening portions can also be rotated by hand in order to transfer the receiving state AUZ into the locked state ARZ, for example for demonstration without receiving a component 5. FIG. 4 shows the state in which the transfer from the receiving state AUZ into the locked state ARZ has been completed. The fastening portions 32 are accordingly facing one another once the transfer from the receiving state AUZ into the locked state ARZ has been completed.

The deformable portion 30a, which is part of the contact portion 30c and consists of a material which has deformable and flexible characteristics, is deformed as a consequence of the rotation of the fastening portions 32 and in particular of the pressure that is exerted via the component 5. The deformable element 30 in the locked state ARZ preferably has a curvature which generally has substantially the same direction with reference to the radius of the curvature as the recess of the frame 12. The deformable element 30 correspondingly assumes a curved state in the locked state ARZ. The deformable element 30 preferably realizes a substantially closed (e.g. circular) receiving means around the component 5. As an alternative to this, the curvature can also assume another form and in particular substantially the form of the respective component 5 which has been received.

In a particular embodiment, the deformable element 30 can be an element which is designed for the purpose of receiving and mounting components 5 with different forms and/or cross-sectional surfaces and/or diameters D. Such forms of the component 5 include round, angular, edged or other forms. To this end, the deformable element 30 can be realized from a material which has not only deformable characteristics but also, in particular, elastic or flexible characteristics. As an alternative to this, the deformable element 30 can be realized on the contact portion 30c which moves into contact with the component 5 at least in part, from multiple partial portions which are connected to one another by one or multiple elastic connection portions (not shown). These can be, for example, rubber connection parts or rubber belts. If an element 5 with a larger diameter D or cross section is to be received, the deformable element 30 can thus then expand or deform correspondingly on account of the elastic characteristics and can adapt to the object or the component 5 to be received.

The deformable element 30, as an alternative to this or in addition to it, can also include required bending points which then bend or fold in the locked state ARZ. In this case, the deformable element 30, on the contact portion 30c, can also be realized by materials which do not necessarily have deformable characteristics. The required bending point or the required bending points and consequently connected deformable characteristics of the deformable element 30 can be ensured as a result of the material being connected at said point by a deformable material, e.g. a rubber belt, or the material being tapered at said point or a hinge-like connection of elements being provided. In said alternative locked state ARZ, the deformable element 30 correspondingly assumes a bent or a folded state.

In the locked state ARZ, the deformable element 30 is deformed in such a manner that a distance between the respective fastening portions 32 is smaller than the distance between the fastening portions 32 in the receiving state AUZ and/or smaller than an outside diameter D (or an outside dimension of the component 5 transversely to the direction q) such that the component 5 is fixed or (fixedly) mounted by the carrier 10 at least in part inside the recess 16. In this connection, the deformable element 30 surrounds the component 5 at least in part and contributes to the fixing. It is also conceivable for the fastening portions 32 to contact one another in the locked state ARZ. The distance between the fastening portions 32 depends, in particular, on a distance between the respective rotational axes or pivot points DP, on a radial dimension of the fastening portions 32 away from the respective rotational axes or pivot points DP and/or on an extent of the deforming of the deformable element 30 in the direction q.

In the locked state ARZ, the contact portion 30c surrounds the component 5 over the contact surface 30d in at least a partially contacting manner. In this case, the one or multiple structural elements 34 (e.g. elevations) can form pressure points on the deformable element 30 which contribute to better fixing of the component 5. Depending on how strong the pressure is at said pressure points, it is possible for the component 5 to be able to be displaced along its longitudinal axis L or along the guide direction. Consequently, it is, for example, possible when laying hoses 5a or cables 5b or other components 5 for the component 5 to remain fixed in its position (corresponding to the x-z plane in FIG. 4), it being able to be reset along the length L where necessary. The guide direction extends substantially along the longitudinal axis L of the component 5 or substantially perpendicularly to the cross-sectional area of the component 5 which is surrounded at least in part by the deformable element 30 in the locked state ARZ. Said cross-sectional surface corresponds in FIG. 4 to the cross-sectional surface of the hose 5a, at the portion which is surrounded in part by the deformable element 30. Said cross-sectional area lies substantially in the plane which is the x-z plane in FIG. 4. The guide direction accordingly corresponds substantially to the y direction shown in FIG. 4. The component 5 of the installation 1 is guided correspondingly through the recess 16 of the frame 12 when it is received at least in part by the deformable element 30 and mounted. At the same time, the component 5 is fixed in such a manner by the mounting system 4 that any slipping, sliding or displacing, possibly triggered by vibrations of the installation, is prevented. The invention is, however, not restricted to components 5 which have a longitudinal axis L. Other objects which are not laid but are only held can also be fixed by the described mounting system 4. Such objects can be, for example, receptacles for delivering substances.

The locked state ARZ, where required, when, for example, the component 5 of the installation 1 is to be released again from the fixing in the carrier 10, can be transferred again into the receiving state AUZ (or displaced toward said state), the component 5 being released again by the deformable element 30. To this end, a force has to be exerted either on the component 5 in the direction opposite the recess 16 (in FIG. 4 characterized by an arrow q'), or however, a force or a torque, which is applied directly to at least one of the fastening portions 32, has to trigger the rotational movement of the fastening portions 32 in the direction opposite the recess 16 (characterized in FIG. 4 by two arrows u' and v').

Figure 5:
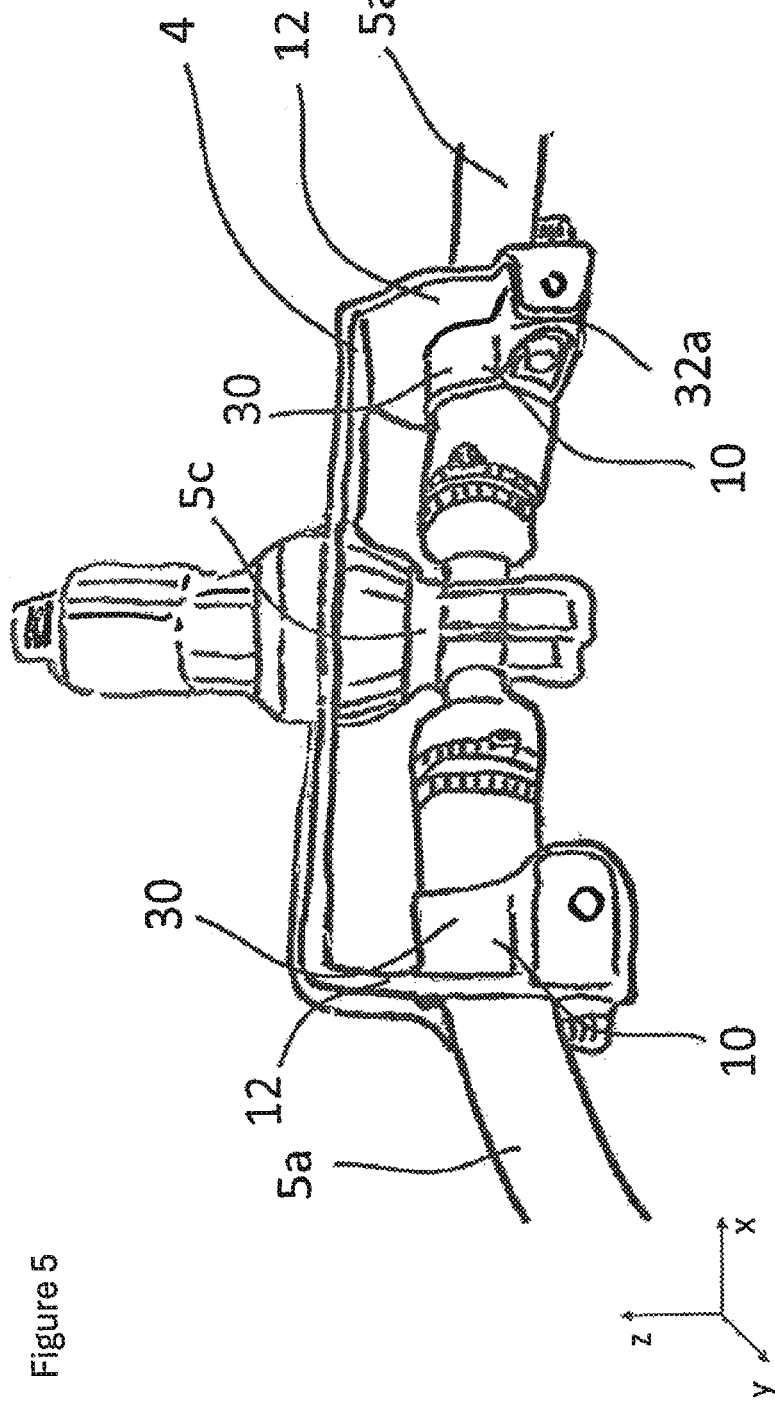
FIG. 5 is a schematic exemplary representation of carriers used in combination with hoses and a pressure sensor.

FIG. 5 shows a schematic representation of the use of two carriers 10 (in the present case shown in the locked state ARZ) in combination with a pressure sensor 5c as an example. The component 5 to be mounted is a hose 5a in FIG. 5. The mounting system 4 includes a plate 20, which connects the respective frames 12 of the carriers 10 together. The plate 20 can be realized for this purpose in one part with the frame 12 of the carrier 10 or can be connected to the frame 12 as a separate element. The plate 20 is preferably formed from a metal. As an alternative to this, it is possible to connect more than two carriers 10 by such a plate 20. The mounting system 4 can be attached to the installation 1 by means of the plate 20. FIG. 5 also shows a pressure sensor 5*c* attached to the mounting system 4. The pressure sensor measures, at a certain portion of the hose 5*a*, the pressure which is built up by the flow or the current of a liquid through the hose 5*a*. As an alternative, instead of this or in addition to it, other elements 5 can also be mounted on the mounting system.

Vibrations on the hose parts or portion of the hose or of the hoses 5*a* which are mounted by the carriers 10, can be adsorbed by the carriers 10 at least in part. Said embodiment makes it possible additionally to assemble portions of the system or of the arrangement outside the installation 1 and then to attach them subsequently to the installation 1. Handling when laying components 5 of the installation 1 is considerably simplified as a result.

Figure 6:
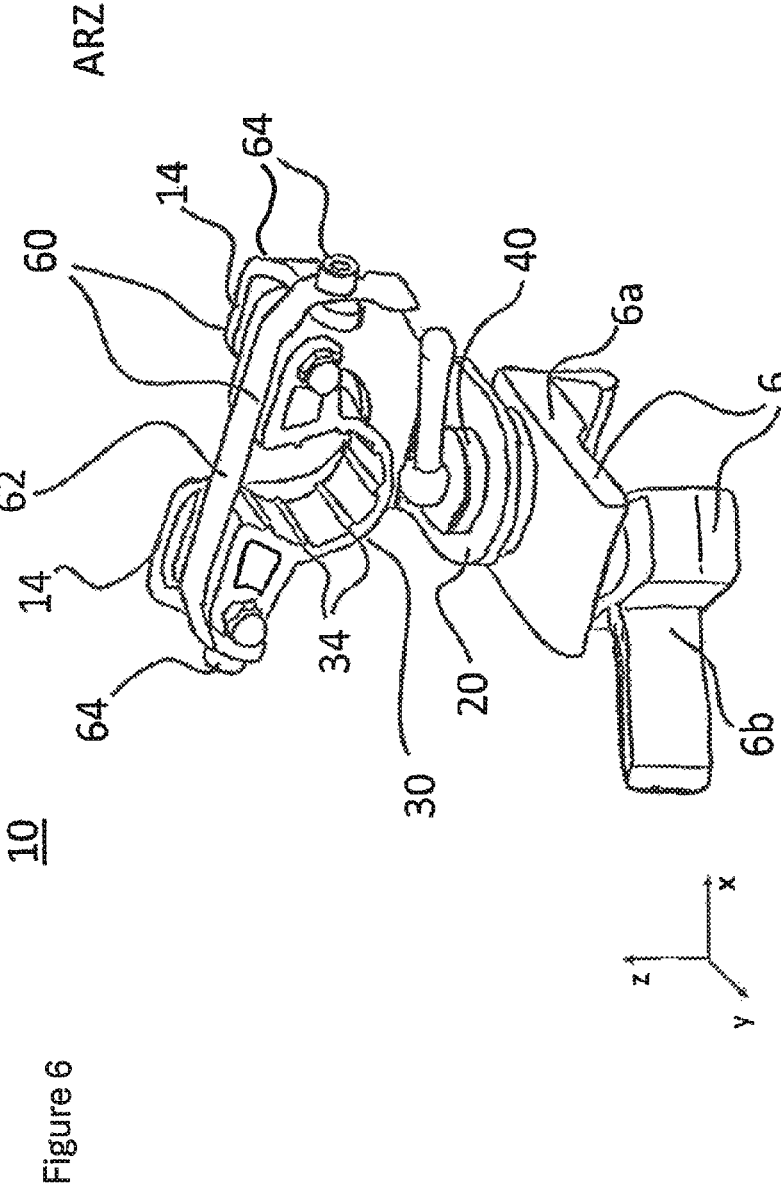
FIG. 6 is a perspective rear view of a carrier in the locked state with a belt as a safety element.

FIG. 6 is the rear view of a mounting system 4 including a carrier 10 in the locked state ARZ with an additional safety function to be used as an option and at least one corresponding safety system 60. The safety system 60 includes, in the present representation, a belt 62 and a fastening device 64. The mounting system 4 shown is certainly present in the locked state ARZ, but in said FIG. 6 for a demonstrative representation has not received any fixed components 5. The safety system 60 serves for additional protection which is to prevent the deformable element 30 transferring inadvertently from the locked state ARZ into the receiving state AUZ and consequently releasing the fixing of the component 5 by the mounting system 4. This could be triggered, for example, by (massive) vibrations or by an inadvertent movement of an operator. The safety system 60 or the safety elements 60 include a belt 62 as shown in FIG. 6 which is preferably a rubber belt or an elastic element.

For safety, the belt 62 is placed over the portion of the deformable element 30 which has a partial portion, which, as shown in FIG. 6, does not surround part of the component 5 or at least cannot exert any pressure onto part of the component 5 in said portion. The two ends of the safety element 60 can be attached by means of a fastening device 64 (e.g. screws) to (in particular respective projections of) the two arms 14 of the frame 12.

As shown in FIG. 6, the belt 62 is then tightened over the surfaces of the two legs 32*a* remote from the recess 16 and the portion which does not surround the component 5 such that unwanted rotation of the legs 32*a* is prevented by the pressure and/or the reinforcing torque which is generated as a result and is produced when the belt 62 is attached. In addition, the belt 62 surrounds or closes the portion of the component 5 (in particular mechanically) which is either not surrounded by the deformable element 30 or which does not exert at least any pressure on the component 5 in said portion.

The fastening device 64 can be realized in one part with the frame 12 or can be an additional separate safety element 60, the safety element 60 being able to be attached on the frame 12, for example bonded on or screwed on. The belt 62 can be connected at least at one of its ends reversibly to the fastening device 64 by a clip or a screw with a pressure surface. For the case where only one end of the belt 62 is connected reversibly to the fastening device 64, the other end can be fixedly or permanently or irreversibly connected to the fastening device 64, e.g. adhesively. As an alternative to this or in addition to it, the safety system 60 can comprise a clamp (not shown) which spans the fastening portions 32 and fixes them in the locked state ARZ.

Figure 7:
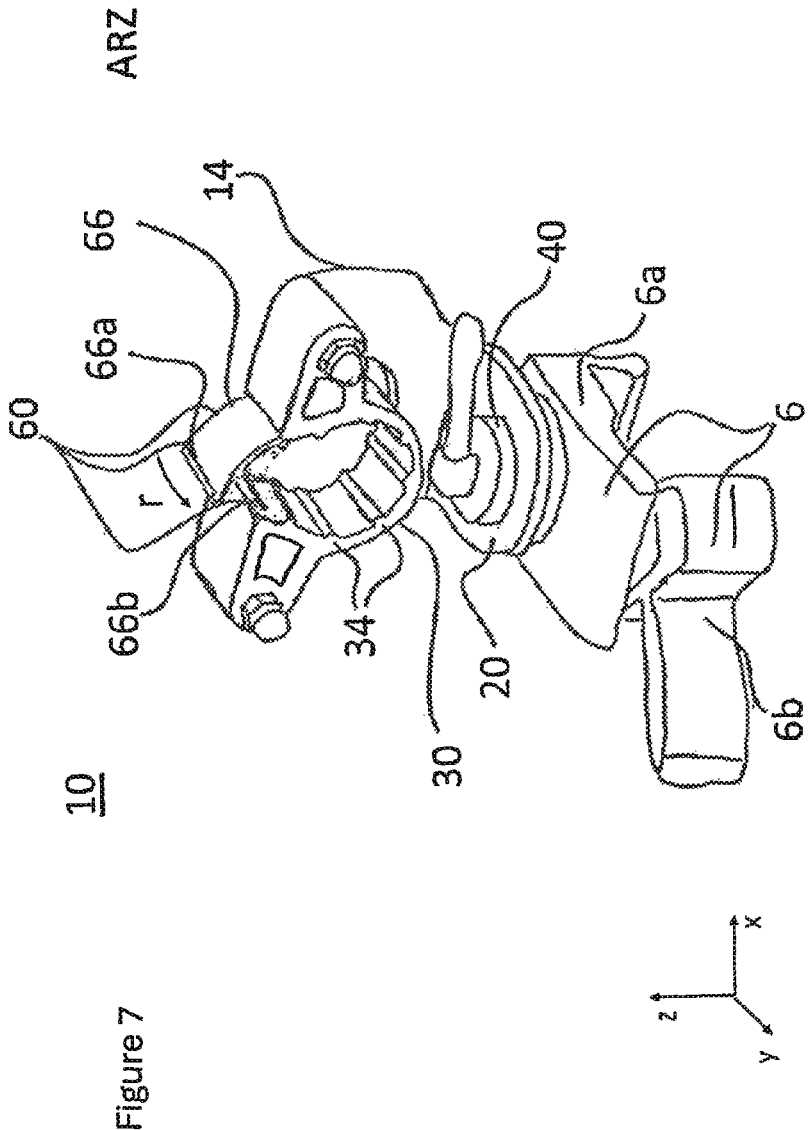
FIG. 7 is a perspective rear view of a carrier in the locked state with a bracket as a safety element and FIG. 8 is a schematic representation of the outside of an installation according to a further embodiment.

FIG. 7 is the rear view of a further mounting system 4 including a carrier 10 in the locked state ARZ with an alternative or additional safety function which can be used as an option and a corresponding safety system 60. In the present embodiment, the safety system 60 includes, in contrast to FIG. 6, at least one bracket 66. The bracket 66, in this case, can be realized in one part or integrally with the deformable element 30 or can be attached or attachable as a separate element on at least one of the ends of the deformable element 30.

If the bracket 66 is to be attached subsequently to both ends of the deformable element 30 by a user, the bracket 66 can be realized in the form of a clip or a clamp. The clamp 66 can be inserted or clamped, for example, between the two legs 32*a*. For the case where the bracket 66 is attached in a non-permanent manner to at least one end of the deformable element 30, the bracket 66 can include a hook and/or an eye system. The system consists, for example, of a hook 66*a* and the hook counterpart 66*b* thereof which, in turn, can be a hook. The hook 66*a* and the hook counterpart 66*b*, in this case, can be attached in each case on an end of the safety bracket 66 and an end, to be connected, of the contact surface 30*d*, and can fix the bracket 66 selectively in a closed arrangement. The bracket 66 can then be reversibly connected on at least one of its two ends by hook 66*a* or by eye to at least one end of the deformable element 30, on which in each case at least one counterpart to the hook 66*b* or to the eye is attached.

As shown in FIG. 7, said connection is effected by bending or folding-over or displacing the bracket 66 in the direction of the recess 16 of the frame 12. The direction of bending or displacing the bracket 66 is characterized in FIG. 7 by the reference symbol r and the corresponding arrow. Once the connection has been closed by the two hooks and/or eyes 66*a*/66*b*, the bracket 66 surrounds or closes the portion of the component 5 which is either not surrounded by the deformable element 30 or does not exert at least any pressure on the component 5 in said portion.

The closed connection of the hooks and/or eyes 66*a*/66*b* prevents the two fastening portions 32 from carrying out an unwanted rotational movement and consequently the locked state ARZ transferring into the receiving state AUZ, the fixing of the component 5 by the mounting system 4 inadvertently being lost. If, for example, two hooks 66 *a/b* are hooked into one another, the connection can thus not be eliminated simply by pulling both portions connected by the hooks 66*a/b* in opposite directions. Such pulling in opposite directions occurs, for example, if a torque were to act on the fastening portions 32 and consequently trigger "untwisting" or opening of the locked state ARZ if no additional safety element 60 were to be provided. This is prevented, however, for the named reason by the hook connection.

By the bracket 66 having to be bent to close the connection, the bracket includes materials with deformable, in particular flexible characteristics for safety 66. The bracket 66 can be realized, for example, from the same material as the deformable element 30. As an alternative to this, however, the bracket 66 can also be realized from all other materials which are eligible in general for the deformable element 30.

FIG. 8 shows a schematic representation of a further embodiment of an installation 101 (in particular of a bioreactor). The installation 101 includes a container with an interior of the container 102*a* and a catch basin of the container 102*b*, as well as a container frame 103. The installation 101 additionally includes a door 106 with a door viewing window 106*a*, a door handle 106*b* and a door hinge 106c. Locating feet 105 ensure that the installation 101 can be positioned at its destination in a fixed manner, the height thereof being adjustable where necessary. Thus, for example, the height of the locating feet 105 can be adjusted in such a manner that the weight of the installation 101 rests thereon, or the height of the locating feet 105 can be reduced in such a manner that the installation 101 rests on the rollers 107. The rollers 107 make it possible for the user to move or to roll the installation 101 to a different site. A bottom window 108 makes it possible for the user to look into the interior of the installation 101 so that he can assess the operation therein or can determine whether matter is situated in the installation 101 or not. In addition, a stirring device 109 is attachable to the installation 101, which stirring device can stir or mix the matter or the substance or substances inside the installation 101.

At least one cable guide 110, which is arranged in a preferred manner to the side and/or above the installation 101 and is fastened (directly or indirectly) on the same, makes it possible to guide cable 5b and or other lines, such as, for example, hoses 5a, along the installation 101 to their destination. For the additional fixing of one or multiple components 5 (such as a hose 5a, a cable 5b, a hose or the like), one or multiple above-described carriers 10 can be attached on or to the cable guide 110.

In addition, the installation 101 includes, in particular, at least one system rail 104 which can serve as a fastening system 6 for components 5 of the installation 101. Thus, for example, a component 5 or multiple components 5 of the installation 101 can be attached on and/or in the installation 101 directly or indirectly via one or multiple counterparts of the system rail 104, for example via sliders or jaws 6a. The system rail 104, in this case, is realized, in particular, such that it guides a slide and/or a jaw 6a along a strip. The slide and/or the jaw 6a include a claw and/or a projection, which are guided or conducted along a recess of the rail. As an alternative to this, the system rail 104 can include a claw and/or a projection which engage in each case in a recess of the slide or of the jaw 6a to be guided. In addition, the counterpart of the system rail 104 includes, in particular, at least one locking or fixing device which locks or fixes the counterpart to the system rail 104 when operating or locking such that further movement along the system rail 104 is prevented.

The system rail 104 can be designed for the purpose of attaching and/or fixing a plurality of different counterparts and/or different components 5 to the installation 101. For example, it is possible to attach a sensor device (not shown) (as a preferred component 5) via corresponding carriers 10 in such a manner in front of the bottom window 108 that the sensor device is able to perform corresponding (e.g. optical) measurements of the content of the installation 101.

Where required, the position at which the component 5 is fixed can be modified by releasing and displacing the carrier/carriers 10 along the system rail 104. The system rail 104 can be attached to the installation 101 in an adhesive and/or screw-connected manner and/or via another fixing mechanism, for example magnetically. The system rail 104 is preferably realized from a metal or steel but can include a polymer or another plastics material and/or be realized from elements of various named materials.

Any elements of all the embodiments of the installation 1, 101 can each have a predetermined color and be subject to a color code. For example, the deformable elements 30 can indicate by a color code which forms and/or diameters D of the components 5 they are capable of receiving. The color can also display other features, such as, for example, a flow direction through a line, the type of the component 5 which is to be received, or the type of material (for example a liquid and/or a gas) which is to be transported by a line.

In the preceding explanation, the term mounting of components 5 is used. Mounting includes, in this connection, in particular, both the holding or the fixing where the component 5 experiences along its longitudinal axis L, in dependence on the pressure, a fixing which can be possibly be overcome, for example by pulling on the component 5, and also the loose guiding of a component 5 where the component 5 is not fixed along its longitudinal axis L but is simply guided to the destination at which the carrier is situated 10. A fixing of components 5 is preferably obtained with the present invention in such a manner that the component 5, when it is mounted by the carrier 10, is mounted in a fixed or secure and slip-free manner along its longitudinal axis L without any external influence. Depending on the pressure or diameter D of the component 5 or the size of the contact surface 30d of the deformable element 30 and the type of the structural element 34, the component 5 can be displaced or reset by pulling lightly or strongly thereon along its longitudinal axis L.

The expert understands how to realize the various or alternative embodiments shown of individual elements of the mounting system 4 in arbitrary combinations, insofar as they are not mutually exclusive. For example, a carrier 10 can include two alternative safety elements 60 at the same time, for example a belt 62 and a bracket 66.

LIST OF REFERENCES

1 Installation for biotechnological applications
2 Container
2a Interior of the container
2b Container inside wall
2c Inner bottom of the container
3 Container frame
4 Mounting system
5 Component of the installation
5a Hose
5b Cable
5c Sensor
5d Pipe
6 Fastening system
6a Jaw
6b Mounting
7 Entry and/or exit
8 Pump
10 Carrier
12 Frame
14 Arm
16 Recess of the frame
18 Bearing counterpart
18a Thread
18b Closing element
18c Displacement recess
20 Base plate or plate
30 Deformable element
30a Deformable portion of the deformable element
30b Rigid portion of the deformable element
30c Contact portion of the deformable element
30d Contact surface of the deformable element
32 Fastening portion
32a Leg
32b Recess of the leg
32c Bridging region of the fastening portion
32d Strut/strip of the fastening portion

34 Structural element
36 Bearing part
40 Joint
50 Pipe clip
52 Hand screw
60 Safety system or safety element
62 Belt for safety
64 Fastening device
66 Bracket
66*a* Hook
66*b* Hook counterpart
DP Pivot point
D Diameter
L Longitudinal axis
ARZ Locked state
AUZ Receiving state
u Direction of rotation
v Direction of rotation
u' Direction of rotation
v' Direction of rotation
w Direction of rotation
w' Direction of rotation
q Direction of movement
q' Direction of movement
r Closing direction
101 Installation for biotechnological applications
102 Container
102*a* Interior of the container
102*b* Catch basin of the container
103 Container frame
104 System rail
105 Locating feet
106 Door
106*a* Door viewing window
106*b* Door handle
106*c* Door hinge
107 Rollers
108 Bottom window
109 Stirring device
110 Cable guide
x Direction in space
y Direction in space
z Direction in space

The invention claimed is:

1. A method for mounting at least one component on an installation, wherein the method comprises the following steps:

attaching a container and a carrier directly or indirectly to the installation, which includes at least one frame with at least two arms, at least one base plate and at least one deformable element, wherein the deformable element includes fastening portions, and wherein the fastening portions are mounted on the arms of the frame, displacing the component toward the deformable element such that the deformable element is displaced from a receiving state (AUZ), in which the deformable element is ready to receive the component of the installation, toward a locked state (ARZ), as a result of which the deformable element surrounds and mounts the component of the installation at least in part, and mounting at least one of the fastening portions so as to be slidingly rotatable about a pivot point (DP) of a bearing counterpart, which is fixed on at least one of the arms and cannot be rotated in relation to the respective arm, in each case by means of at least one bearing part, which is attached on one of the fastening portions, wherein the bearing part is a continuous bore or recess, wherein the bearing counterpart comprises a pin or a joint or a bolt, and wherein the bearing counterpart is produced from metal or steel and is realized integrally or in one part with the corresponding arm.

2. The method as claimed in claim 1, wherein the method further comprises attaching the base plate of the carrier directly or indirectly to the installation so as to be pivotable via a bearing and/or a belt and/or a joint.

3. The method as claimed in claim 1, wherein the at least one bearing part, is a sliding bearing.

4. The method as claimed in claim 1, wherein the method further comprises arranging a safety element on the frame and/or on the deformable element in order to prevent the opening of the deformable element in the locked state (ARZ).

5. The method as claimed in claim 1, wherein the deformable element includes on its contact surfaces structural elements and/or elevations and/or indentations which are in at least partial contact with the component of the installation.

6. The method as claimed in claim 1, wherein the deformable element is designed for the purpose of receiving and/or mounting and/or fixing components of the installation with various forms and/or diameters (D) or cross-sectional surfaces.

7. The method as claimed in claim 1, wherein at least one element included by the installation comprises at least one color corresponding to a color coding.

* * * * *